United States Patent [19]

Punian

[11] Patent Number: Plant 7,168

[45] Date of Patent: Feb. 27, 1990

[54] FRENCH PRUNE (PUNIAN)

[76] Inventor: Gurbachan Punian, 1351 Debbie La., Yuba City, Calif. 95991

[21] Appl. No.: 259,340

[22] Filed: Oct. 17, 1988

[51] Int. Cl.[4] ..... A01H 5/00

[52] U.S. Cl. ..... Plt./38

[58] Field of Search ..... Plt./38

[56] References Cited

U.S. PATENT DOCUMENTS

| | | | |
|---|---|---|---|
| P.P. 4,232 | 4/1978 | Friedman et al. | Plt. 38 |
| P.P. 4,417 | 2/1979 | Hickerson | Plt. 88 |
| P.P. 5,583 | 3/1985 | Blickenstaff | Plt. 30 |

OTHER PUBLICATIONS

Childers, N. F., "Chapter 15: Culture of Plums", *Modern Fruit Science,* 4th Ed., Horticultural Publications, Rutgers Univ. (1969), pp. 392–395.

*Primary Examiner*—James R. Feyrer
*Attorney, Agent, or Firm*—Bernhard Kreten

[57] ABSTRACT

A new asexually developed French prune cultivar to be known as 'Punian' Prune which is of large to medium size, dense, upright, vase formed, very similar to the regular French prune tree; the tree is distinguished from regular French Prune by faster maturity to the fruit bearing stage. The fruit has the same basic color skin, flesh, texture and stone as regular French prune, however it is characterized by higher sugar content of the fruit.

2 Drawing Sheets

ORIGIN OF VARIETY

The present variety of prune ("Punian") was discovered by inventor, on a tree in his orchard planted to regular French prune. The inventor, an orchardist, upon inspection and maintanence of his orchard took particular note of the distinct characteristics of such atypical prune tree and realized that such characteristics would be of significant advantage in a prune tree for commercial production.

CLASSIFICATION OF THE VARIETY

The present new and distinct variety of prune tree is embraced by Plant Patent Sub-Class 38, of the U.S. Patent Office Manual of Classification.

ASEXUAL REPRODUCTION OF THE VARIETY

A number of the present variety of prune trees were asexually reproduced on inventor's behalf by a commercial nursery by grafting on Mariana rootstock. A plot of 12 trees was planted in inventor's orchard in February 1982. The botanical characteristics of the 'Punian' variety appear the same as the parent regular French prune. However, asexual reproduction of the 'Punian' variety produced early maturing fruit of increased sugar content consistent with the original bud sport.

SUMMARY OF THE VARIETY

The present variety of prune trees, to be known as the "Punian" prune is, characteristically, a vigorous grower of large to medium size, an upright dense, vase formed hardy tree. It is foliated in medium sized, ovate, somewhat thick and slightly rough wrinkled deep green leaves. It produces a crop of medium sized smooth texture semi-cling skin fruit, basically the same as regular French prune. Fruit ripens approximately 15–18 days earlier than regular French prune (depending somewhat on growing conditions and cultivation practices). Additionally, the sugar content (30–31%) is higher than the regular French prune at harvest. The skin color is basically the same as regular French prune: deep blue and flesh color yellow to amber. The present variety has a higher soluble sugar content than regular French prune which makes this variety particularly suitable for commercial production.

The present variety of prune tree is further, and more particularly, characterized in the following respects:

The tree develops very similarly to regular French prune. It is large to medium with vigorous upright growth. Pruning methods and cultivation practices basically determine size and shape. The trunk and branch texture are generally smooth. Leaves are ovate, dark green, slightly wrinkled and of medium average length and width. Margins are of medium fine serration. Flower buds are white, conical shaped which flatten at full bloom. The tree comes into full bloom at the same time as regular French prune. Punians' pollination requirements are the same as regular French prune. It is a self-pollinated variety that is self-fruitful. Fruit size, texture color and stone are the same as regular French prune: ovate shaped fruit with pronounced cavity, medium size with medium thick, smooth skin texture that is semi-cling with down wanting. Flesh is a medium soft-texture with soft, tender fibers and a rich sweet flavor and mild aroma. The present variety matures and ripens approximately 15–18 days before regular French Prune. The stone is medium size to small, light brown cling. Pits small and wanting. Form elliptical.

Field trials indicate fruit average fresh weight 21–24 grams each; average dry weight 8.8–9.2 grams each; and 50–54 dry fruit per pound.

The fruit can be used as fresh fruit, for canning and for drying.

Early maturation and high sugar content make the "Punian" prune a superior improvement over the regular French prune and its varieties. The high percent of soluble sugars result in a prune of increased plumpness.

BRIEF DESCRIPTION OF THE DRAWING FIGURES

One drawing is an illustration, by photographic reproduction, in color of limb with leaves a fruit cut open to show flesh and pit. Another drawing depicts a limb with the tree in bloom and with flower detail.

RESISTANCE TO INSECTS AND DISEASE

Comparable to regular French prune. Slight increased nematode resistance exists due to grafting on the Mariana root stock.

The prune tree and its fruit herein described may vary in slight detail due to climatic and soil conditions under which the variety may be grown; the present trees were grown in Sutter County (Sacramento Valley), Calif.

It is claimed:

1. A new and distinct French prune substantially as illustrated and described, particularly characterized by its upright, vase shaped tree form of medium to large size; its vigorous growth; by reaching full maturity earlier than other varieties of French prune; and by bearing excellent fruit with a high sugar content which are particularly suitable for commercial production.

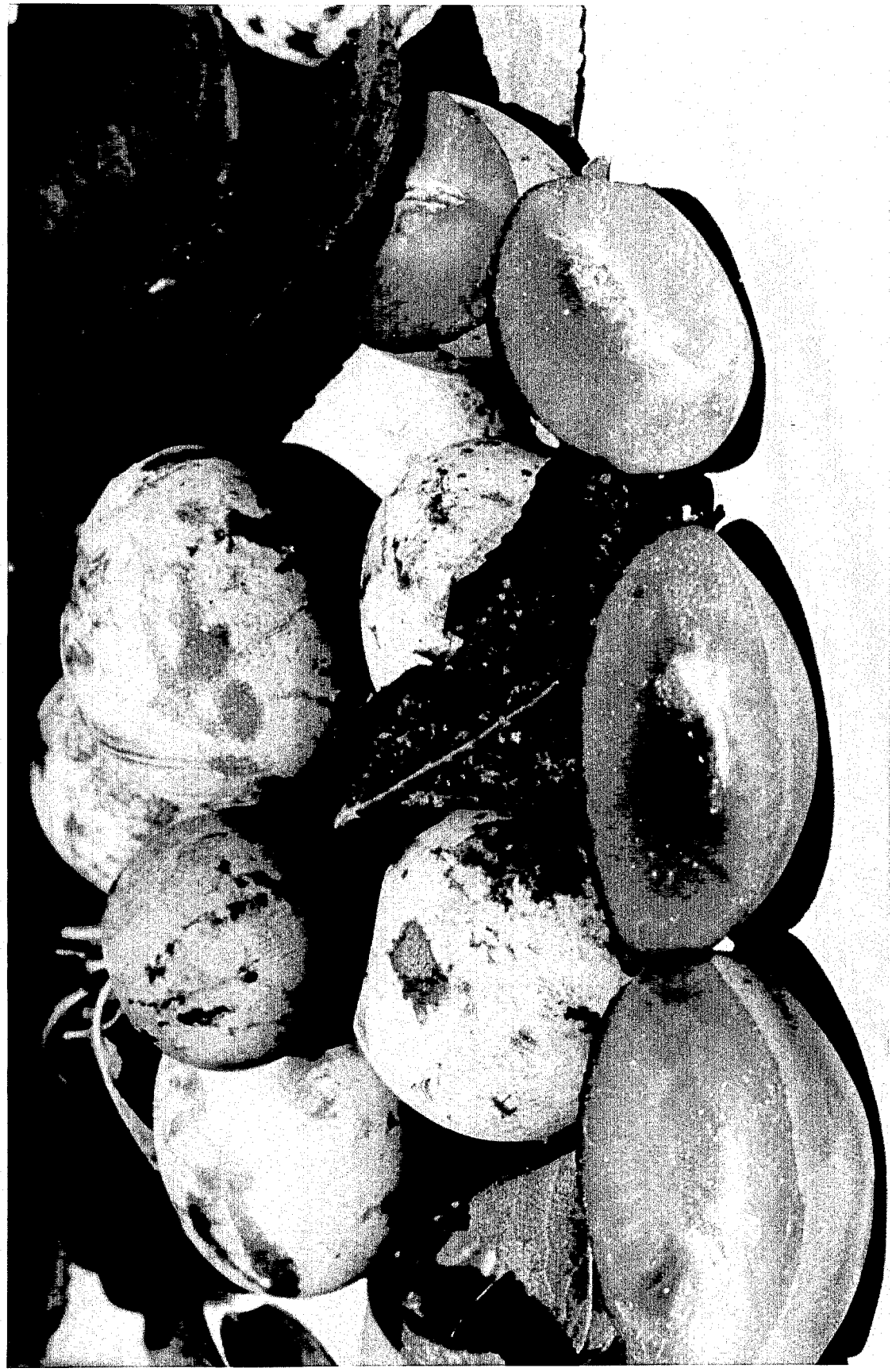

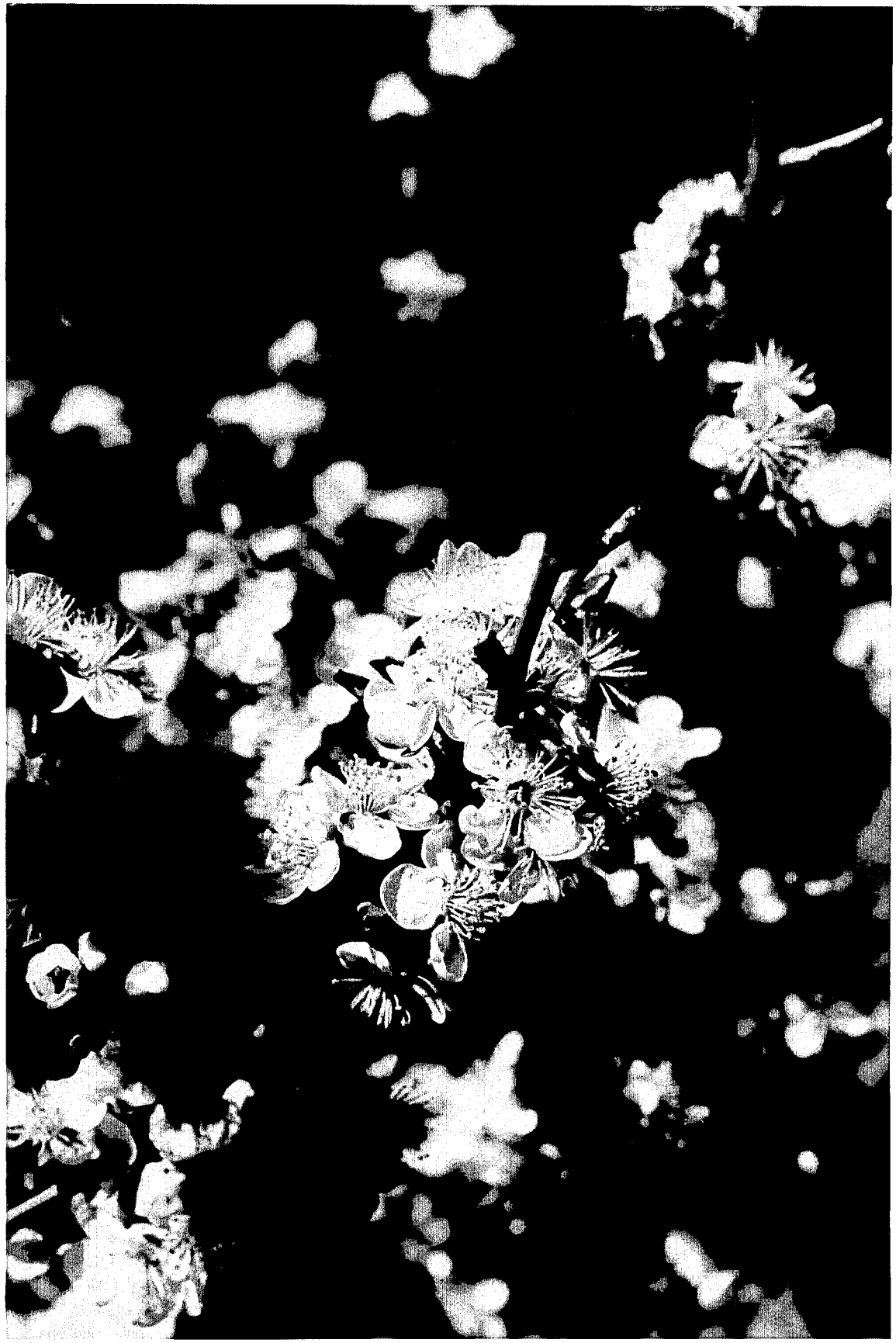

* * * * *